(12) United States Patent
Moon et al.

(10) Patent No.: US 9,415,377 B1
(45) Date of Patent: Aug. 16, 2016

(54) CU-BASED CATALYST SUPPORTED ON COMPLEX METAL OXIDE STRUCTURES HAVING MESO- AND MACROPORES FOR PREPARING 1, 2-PROPANEDIOL

(71) Applicant: KOREA INSTITUTE OF SCIENCE AND TECHNOLOGY, Seoul (KR)

(72) Inventors: Dong Ju Moon, Seoul (KR); Jae Sun Jung, Seoul (KR); Sang Yong Lee, Seoul (KR); Ji In Park, Seoul (KR); Kwang Hyeok Lee, Seoul (KR); Sea on Lee, Seoul (KR); Sung Soo Lim, Seoul (KR); Gi Hoon Hong, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/920,076

(22) Filed: Oct. 22, 2015

(30) Foreign Application Priority Data

May 15, 2015 (KR) ........................ 10-2015-0067964

(51) Int. Cl.
| | |
|---|---|
| *B01J 23/70* | (2006.01) |
| *B01J 23/72* | (2006.01) |
| *B01J 23/78* | (2006.01) |
| *B01J 23/00* | (2006.01) |
| *B01J 35/10* | (2006.01) |

(52) U.S. Cl.
CPC ................ *B01J 23/78* (2013.01); *B01J 23/002* (2013.01); *B01J 23/72* (2013.01); *B01J 35/1038* (2013.01); *B01J 35/1042* (2013.01); *B01J 35/1047* (2013.01); *B01J 35/1061* (2013.01); *B01J 35/1066* (2013.01); *B01J 35/1071* (2013.01); *B01J 35/1076* (2013.01)

(58) Field of Classification Search
CPC ........ B01J 23/72; B01J 23/78; B01J 35/1061; B01J 35/1042; B01J 35/1066; B01J 35/1076; B01J 35/1071; B01J 35/1038; B01J 23/002; B01J 35/1047
USPC .......................................................... 502/346
See application file for complete search history.

(56) References Cited

U.S. PATENT DOCUMENTS

2010/0312024 A1   12/2010   Henkelmann et al.

FOREIGN PATENT DOCUMENTS

| JP | 2007-283175 A | 11/2007 |
|---|---|---|
| JP | 2008-266234 A | 11/2008 |
| JP | 2012-188390 A | 10/2012 |
| KR | 1020110116480 A | 10/2015 |

OTHER PUBLICATIONS

Zhenle Yuan et al. "Hydrogenolysis of glycerol over homogenously dispersed copper on solid base catalysts" Applied Catalysis B: Environmental vol. 101, Issues 3-4, pp. 431-440, Oct. 20, 2010.*

* cited by examiner

*Primary Examiner* — Colleen Dunn
*Assistant Examiner* — Haytham Soliman
(74) *Attorney, Agent, or Firm* — Ladas & Parry LLP

(57) ABSTRACT

The present invention relates to a copper-based catalyst for preparing 1,2-propanediol, wherein copper as an active metal is supported on a complex metal oxide structure having mesopores and macropores at the same time, a method for preparing the copper-based catalyst, and method for selectively preparing 1,2-propanediol from dehydration and hydrogenation of glycerol using the copper-based catalyst.

3 Claims, 3 Drawing Sheets

CU-BASED CATALYST SUPPORTED ON COMPLEX METAL OXIDE STRUCTURES HAVING MESO- AND MACROPORES FOR PREPARING 1, 2-PROPANEDIOL

CROSS-REFERENCE TO RELATED APPLICATIONS

This application claims, under 35 U.S.C. §119, the priority of Korean Patent Application No. 10-2015-0067964, filed on May 15, 2015, in the Korean Intellectual Property Office, the disclosure of which is incorporated herein by reference in its entirety.

BACKGROUND (a) Technical Field

The present invention relates to a copper-based catalyst for preparing 1,2-propanediol, wherein copper as an active metal is supported on a complex metal oxide structure having mesopores and macropores at the same time, a method for preparing the copper-based catalyst, and method for selectively preparing 1,2-propanediol from dehydration and hydrogenation of glycerol using the copper-based catalyst.

(b) Background Art 1,2-Propanediol is a compound used as raw materials and intermediates of various chemical products such as antifreezes, surfactants, synthetic resins, etc. In general, the 1,2-propanediol is prepared from glycerol which is obtained as a byproduct in the production process of biodiesel.

Glycerol is one of the byproducts obtained during biodiesel production and, at present, it is used as raw materials of cosmetics, soaps, etc. Recently, the production of biodiesel as environment-friendly alternative energy is increasing rapidly. Consequently, its byproduct glycerol is also produced in larger quantities than its demand. Therefore, research has been actively carried out on the synthesis of valuable 1,2-propanediol using the glycerol produced as the industrial byproduct.

The catalytic reactions for synthesizing 1,2-propanediol from glycerol known thus far are as follows.

Japanese Patent Publication No. 2008-266234 (patent document 1) discloses a method of preparing 1,2-propanediol from dehydration and hydrogenation of glycerol by adding the cation exchange resin Amberlyst® 15 and Amberlyst® 70 to a catalyst in which ruthenium is impregnated in activated carbon. Here, the amount of the cation exchange resin is twice as many as the catalyst.

US Patent Publication No. 2010-0312024 (patent document 2) discloses a method of preparing 1,2-propanediol from glycerol in the presence of a catalyst prepared by mixing copper oxide with a metal oxide such as zinc oxide at a specific ratio.

Japanese Patent Publication No. 2007-283175 (patent document 3) discloses a method of preparing 1,2-propanediol from glycerol in the presence of a catalyst prepared by impregnating ruthenium in a basic metal oxide (e.g., MgO, $ZrO_2$, etc.).

Korean Patent Publication No. 10-2011-0116480 (patent document 4) discloses a method of preparing 1,2-propanediol from glycerol using a catalyst wherein the noble metal ruthenium as a group VIIIB element is supported on a hydrotalcite-like support in which group IIA and group IIB metal elements are coprecipitated.

Japanese Patent Publication No. 2012-188390 (patent document 5) discloses a method of preparing 1,2-propanediol from glycerol using a catalyst prepared by reducing hydrotalcite containing a divalent metal element and a trivalent metal element.

The present invention provides a novel copper-based supported catalyst which exhibits high catalytic activity for dehydration and hydrogenation of glycerol, wherein copper as an active metal is highly dispersed and supported on a complex metal oxide structure having mesopores and macropores at the same time as a support.

REFERENCES OF THE RELATED ART

Patent Documents (Patent document 1) Japanese Patent Publication No. 2008-266234 "Method for reducing glycerol".

(Patent document 2) US Patent Publication No. 2010-0312024 "Method for producing 1,2-propanediol by low-pressure hydrogenation of glycerin".

(Patent document 3) Japanese Patent Publication No. 2007-283175 "Catalyst for reduction of glycerol and method of manufacturing 1,2-propanediol".

(Patent document 4) Korean Patent Publication No. 10-2011-0116480 "Noble metal catalyst supported on complex metal oxide support and method for manufacturing 1,2-propanediol using the same".

(Patent document 5) Japanese Patent Publication No. 2012-188390 "Method for producing 1,2-propanediol"

SUMMARY

The present invention is directed to providing a copper-based catalyst for synthesis of 1,2-propanediol from dehydration and hydrogenation of glycerol, wherein copper as an active metal is supported on a complex metal oxide structure having meso- and macropores.

The present invention is also directed to providing a method for preparing a catalyst for synthesis of 1,2-propanediol by supporting copper as an active metal on a complex metal oxide structure having meso- and macropores at the same time as a support, which has been prepared by coprecipitating $Mg_6Al_2O_8$ as a metal oxide having mesopores and aluminum- and silicone-based inorganic binders and conducting hydrothermal synthesis.

The present invention is also directed to providing a method for preparing 1,2-propanediol from glycerol using a novel copper-based catalyst which suppresses the production of ethylene glycol as a byproduct while maintaining glycerol conversion rate and 1,2-propanediol selectivity high.

In an aspect, the present invention provides a copper-based catalyst for synthesis of 1,2-propanediol, wherein copper as an active metal is supported on a complex metal oxide structure having meso- and macropores represented by Chemical Formula 1, which has been prepared by coprecipitating $Mg_6Al_2O_8$ as a metal oxide having mesopores and aluminum- and silicone-based inorganic binders.

$$Al_8—Si_y—Mg_6Al_2O_8 \quad \text{[Chemical Formula 1]}$$

In Chemical Formula 1, x or y is the molar ratio of coprecipitated Al or Si per 1 mol of the $Mg_6Al_2O_8$ as a metal oxide having mesopores, x satisfying 0<x<25 and y satisfying 0<y<20.

In another aspect, the present invention provides a method for preparing a catalyst for synthesis of 1,2-propanediol, including:

a) a process of preparing $Mg_6Al_2O_8$ as a metal oxide having mesopores by drying and sintering a hydrotalcite structure which has been prepared by coprecipitating an aluminum compound, a magnesium compound and a carbonate compound and conducting hydrothermal synthesis;

b) a process of preparing a complex metal oxide structure having meso- and macropores represented by Chemical Formula 1 by coprecipitating the $Mg_6Al_2O_8$ metal oxide and aluminum- and silicone-based inorganic binders, conducting hydrothermal synthesis, drying and then sintering; and c) a process of preparing a copper-based catalyst by supporting a copper compound on the complex metal oxide structure:

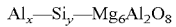

$Al_x$—$Si_y$—$Mg_6Al_2O_8$      [Chemical Formula 1]

wherein x or y is the molar ratio of coprecipitated Al or Si per 1 mol of the $Mg_6Al_2O_8$ as a metal oxide having mesopores, x satisfying 0<x<25 and y satisfying 0<y<20.

In another aspect, the present invention provides a method for preparing 1,2-propanediol, which includes conducting dehydration and hydrogenation of glycerol at a reaction temperature of 190-200° C. and a reaction pressure of 20-30 bar in the presence of the copper-based catalyst.

In the present invention, the complex metal oxide structure having meso- and macropores represented by Chemical Formula 1 is used as a support for supporting copper as the active metal, the selectivity of 1,2-propanediol is improved and the selectivity of ethylene glycol as a byproduct is greatly decreased.

Also, when the copper-based catalyst of the present invention is used for dehydration and hydrogenation of glycerol, glycerol conversion rate of 53% or greater, 1,2-propanediol selectivity of 96.0% or greater and 1,2-propanediol yield of 50.9% or greater can be achieved, and the selectivity of ethylene glycol as a byproduct can be decreased to 1% or lower. As a result, a purification process can be simplified.

DETAILED DESCRIPTION

Figure 1:
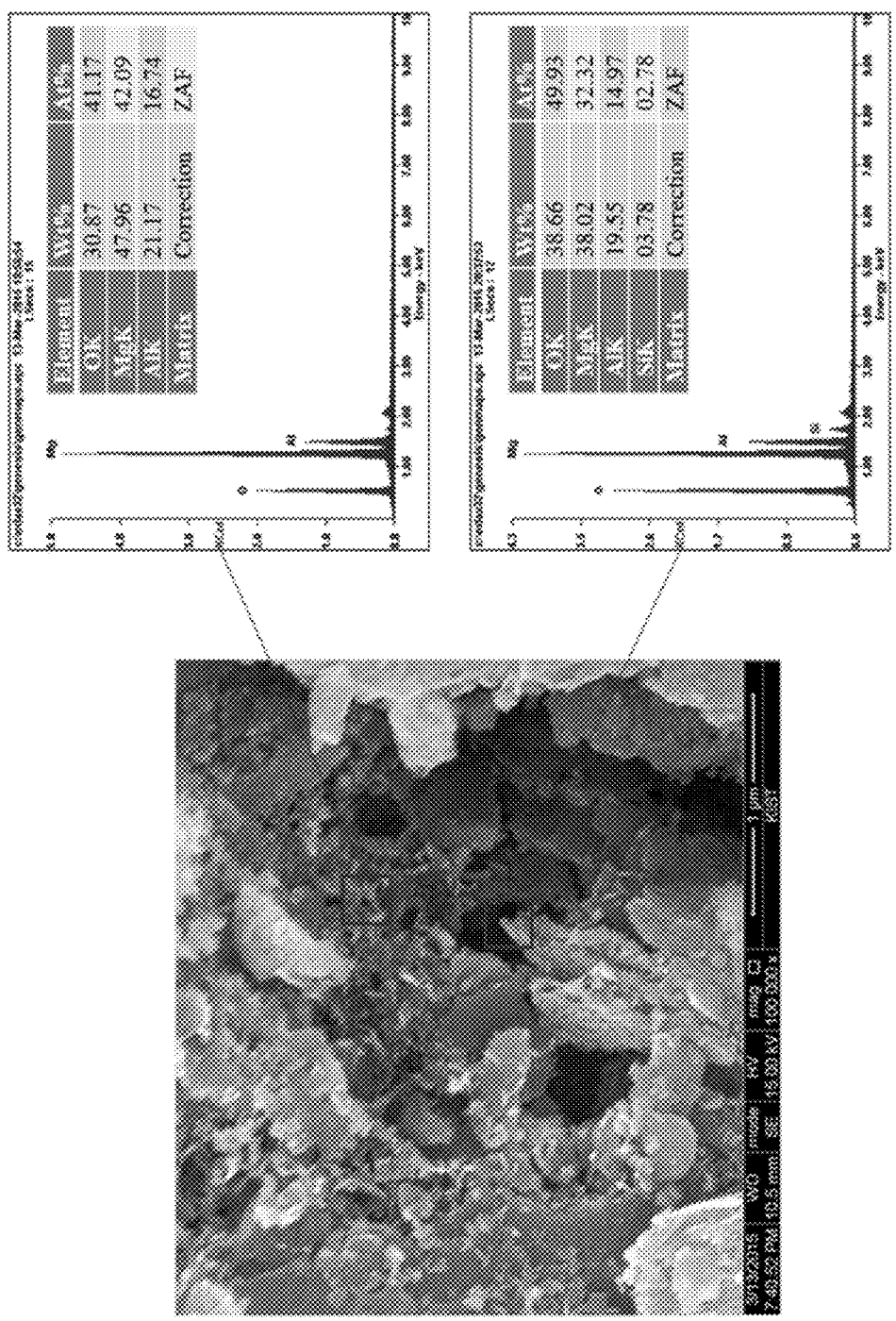
FIG. 1 illustrates an electron microscopic image of a 'complex metal oxide structure having meso- and macropores' used as a support in the present invention.

The present invention relates to a copper-based catalyst for selective preparation of 1,2-propanediol from dehydration and hydrogenation of glycerol, a method for preparing the catalyst, and a method for preparing 1,2-propanediol from glycerol using the catalyst.

The present invention provides a copper-based supported catalyst wherein copper as an active metal is supported on a complex metal oxide structure having meso- and macropores represented by Chemical Formula 1.

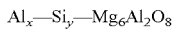

$Al_x$—$Si_y$—$Mg_6Al_2O_8$      [Chemical Formula 1]

In Chemical Formula 1, x or y is the molar ratio of coprecipitated Al or Si per 1 mol of the $Mg_6Al_2O_8$ as a metal oxide having mesopores, x satisfying 0<x<25 and y satisfying 0<y<20.

The complex metal oxide structure used as a support in the present invention has mesopores and macropores at the same time.

The mesopores are present inside the $Mg_6Al_2O_8$ metal oxide and have an average pore size of 24-36 nm and a total pore volume of 0.05-2 cm³/g.

And, the macropores are present between aluminum (Al) and silicone (Si) particles adsorbed on the surface of the $Mg_6Al_2O_8$ metal oxide and have an average pore size of 0.05-4.1 μm and a total pore volume of 0.05-20 cm³/g.

In the copper-based catalyst of the present invention, the copper as the active metal may be supported in an amount of 0.1-20 wt %, specifically 2-10 wt %, based on the weight of the complex metal oxide structure. When the supporting amount of the copper as the active metal is less than 0.1 wt %, only dehydration may occur and hydrogenation may not occur effectively. As a result, the selectivity and yield of 1,2-propanediol may decrease. On the other hand, when the supporting amount of the copper as the active metal exceeds 20 wt %, the selectivity and yield of byproducts such as methane, ethylene glycol, etc. may increase and the cost of catalyst preparation may increase.

The present invention also provides a method for preparing a copper-based catalyst, including:

a) a process of preparing $Mg_6Al_2O_8$ as a metal oxide having mesopores by drying and sintering a hydrotalcite structure which has been prepared by coprecipitating an aluminum compound, a magnesium compound and a carbonate compound and conducting hydrothermal synthesis;

b) a process of preparing a complex metal oxide structure having meso- and macropores represented by Chemical Formula 1 by coprecipitating the $Mg_6Al_2O_8$ metal oxide and aluminum- and silicone-based inorganic binders, conducting hydrothermal synthesis, drying and then sintering; and c) a process of preparing a copper-based catalyst by supporting a copper compound on the complex metal oxide support.

Each process of the method for preparing a copper-based catalyst according to the present invention will be described in detail.

First, the process a) is a process of preparing $Mg_6Al_2O_8$ as a metal oxide having mesopores.

The $Mg_6Al_2O_8$ metal oxide is prepared by a method for preparing a hydrotalcite structure through hydrothermal synthesis. That is to say, a magnesium compound, an aluminum compound and a carbonate compound are coprecipitated at room temperature (15-30° C.) at an adequate ratio and pH is adjusted to 9-11 using an alkaline aqueous solution. Then, a hydrotalcite precursor is prepared by conducting hydrothermal synthesis at 120-230° C. for 1-10 hours. Then, the prepared hydrotalcite precursor is dried at 50-90° C. and sintered at 500-1000° C. to prepare an $Mg_6Al_2O_8$ metal oxide.

As metal precursors used to prepare the $Mg_6Al_2O_8$ metal oxide, the magnesium compound and the aluminum compound may be a nitrate, a sulfate, an acetate, an acetonate, a chloride, etc. Although nitrates are mainly used in the examples of the present invention, the kind of the metal precursors is not particularly limited.

The carbonate compound may be, for example, ammonium carbonate or a carbonate of an alkali metal or an alkaline earth metal such as sodium carbonate, calcium carbonate, etc.

And, the alkaline aqueous solution used to adjust pH when conducting the hydrothermal synthesis may be ammonia water or an aqueous solution containing an alkali metal compound such as sodium hydroxide, potassium hydroxide, etc. The concentration may be controlled adequately in a range of 0.1-5 M.

The $Mg_6Al_2O_8$ metal oxide prepared in the process a) has meso-sized pores inside thereof, having an average pore size of 24-36 nm and a total pore volume of 0.05-2 cm³/g.

The process b) is a process of preparing the complex metal oxide structure used as a catalyst support. The complex metal oxide structure is a structure having meso- and macropores wherein aluminum (Al) and silicone (Si) metal elements are adsorbed on the surface of the $Mg_6Al_2O_8$ metal oxide. That is to say, in the process b), the $Mg_6Al_2O_8$ metal oxide and aluminum- and silicone-based inorganic binders are coprecipitated at room temperature (15-30° C.) at an adequate ratio. Then, pH is adjusted to 9-11 using an alkaline aqueous solution and hydrothermal synthesis is conducted at 120-230° C. for 1-10 hours. Then, the prepared complex metal oxide is dried at 50-90° C. and sintered at 500-1000° C. to prepare the complex metal oxide structure having meso- and macropores represented by Chemical Formula 1.

In the present invention, an aluminum-based binder and a silicone-based binder may be used as inorganic binders. The aluminum-based binder may be, for example, aluminum nitrate, aluminum sulfate, aluminum acetate, aluminum chloride, aluminum acetylacetonate, etc. The silicone-based binder may be, for example, kaolin, bentonite, etc. The inorganic binder may be used by dispersing in water or an organic solvent. Specifically, the organic solvent may be an alcohol such as methanol or ethanol and the silicone-based binder may be dispersed to a concentration of 0.05-5 M, although not being specially limited thereto. The inorganic binder is dispersed in the solvent and turns into a metal hydroxide in the form of an inorganic gel and is adsorbed on the surface of the $Mg_6Al_2O_8$ metal oxide. During the sintering process, the organic component of the adsorbed inorganic binder disappears and only the metal elements Al and Si remain, forming macropores.

The amount of the inorganic binder may be controlled in a range where the requirement for the x and y values in Chemical Formula 1 is satisfied. That is to say, the aluminum-based binder may be added in an amount such that the molar ratio of aluminum (x) per 1 mol of the $Mg_6Al_2O_8$ metal oxide satisfies $0<x<25$. And, the silicone-based binder may be added in an amount such that the molar ratio of silicone (y) per 1 mol of the $Mg_6Al_2O_8$ metal oxide satisfies $0<y<20$. When the molar ratio of the coprecipitated Al or Si per 1 mol of the $Mg_6Al_2O_8$ metal oxide is smaller than the above-described range, a small number of macropores are formed, and used as a catalyst, leading to decreased 1,2-propanediol selectivity. On the other hand, when the molar ratio of the coprecipitated Al or Si is larger than the above-described range, the specific surface area of the support is decreased. As a result, the supporting amount of the copper as the active metal is decreased, leading to decreased catalytic activity.

The complex metal oxide structure prepared in the process b) is a structure wherein the aluminum (Al) and silicone (Si) metal elements are adsorbed on the surface of the $Mg_6Al_2O_8$ metal oxide. And, the pores present between the aluminum (Al) and silicone (Si) particles adsorbed on the surface of the $Mg_6Al_2O_8$ metal oxide are macro-sized pores having an average pore size of 0.05-4.1 μm and a total pore volume of 0.05-20 cm$^3$/g.

FIG. 1 shows an electron microscopic image of the complex metal oxide structure prepared through the process b). From FIG. 1, it can be seen that the aluminum (Al) and silicone (Si) metal elements are adsorbed on the surface of the $Mg_6Al_2O_8$ metal oxide having mesopores. Also, it can be seen that the pores formed between the aluminum (Al) and silicone (Si) pares are macro-sized.

Figure 2:
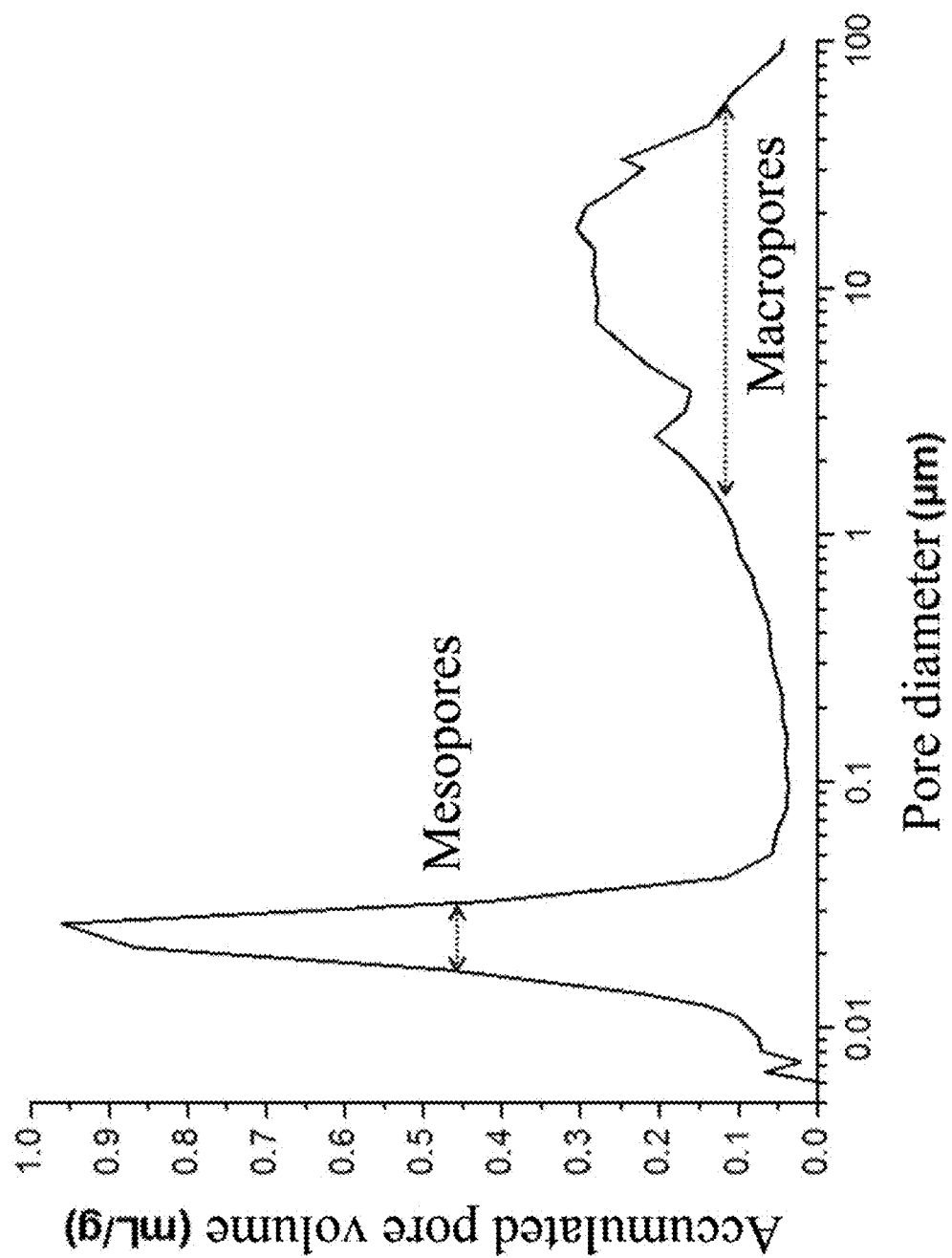
FIG. 2 illustrates a result of analyzing a 'complex metal oxide structure having meso- and macropores' used as a support in the present invention using a mercury porosimeter.

FIG. 2 shows a result of analyzing the complex metal oxide structure having meso- and macropores using a mercury porosimeter. From FIG. 2, it can be seen that the complex metal oxide structure Cu/GP-4 has mesopores (10-40 nm) and macropores (1-50 μm) at the same time.

The process c) is a process of preparing the copper-based catalyst wherein copper as an active metal is supported on the complex metal oxide structure.

The copper as the active metal may be supported by impregnation, coprecipitation, etc. which are commonly used in the preparation of catalysts. The supporting method is not particularly limited in the present invention. As a copper precursor, a nitrate, a sulfate, an acetate, a chloride, etc. may be used. The copper precursor is not particularly limited in the present invention.

The copper as the active metal may be supported in an amount of 0.1-20 wt %, specifically 2-10 wt %, based on the weight of the complex metal oxide structure.

After the copper compound is supported on the complex metal oxide structure, the desired copper-based catalyst of the present invention is prepared by drying at 50-90° C. and sintering at 500-1000° C. The drying may be conducted by slowly evaporating water at 50-90° C. in a water bath and then sufficiently drying the residue in an oven maintained at 50-90° C.

The sintering may be conducted at 500-1000° C., specifically 700-900° C. When the sintering temperature is too low, the active metal copper may not be dispersed well on the catalyst support. On the other hand, when the sintering temperature is too high, surface area may decrease significantly as the catalyst support and the noble metal particles are sintered. Sintering time may be specifically 1-12 hours, more specifically 4-6 hours. When the sintering time is too short, it is highly likely that the copper-based active metal is distributed nonuniformly on the catalyst support. On the other hand, when the sintering time is too long, the surface area of the catalyst may decrease significantly as the support and the noble metal particles are sintered.

The copper-based catalyst prepared by the above-described method has average pore sizes of 24-36 nm and 0.05-4.1 μm. That is to say, unlike the existing copper-based catalyst supported on a hydrotalcite structure, the catalyst has not only mesopores but also macropores.

The present invention also provides a method for 1,2-propanediol from glycerol using the copper-based catalyst.

More specifically, 1,2-propanediol is prepared by conducting dehydration and hydrogenation of glycerol simultaneously and continuously in the presence of the copper-based catalyst and hydrogen. A reactor for synthesizing 1,2-propanediol may be selected from a batch reactor, semi-batch reactor, a continuous circulation reactor, etc. commonly used in the art. In the present invention, selection of the reactor is not particularly limited.

The glycerol used as a reactant may be either high-purity glycerol or crude glycerol containing impurities. For example, crude glycerol obtained during a biodiesel production process may be used. Also, the glycerol may be used as being mixed with a solvent. The solvent is not particularly limited, but one that can be easily separated from 1,2-propanediol and is inexpensive may be used. As a solvent satisfying these requirements, water may be used. When the solvent is used, the concentration of the glycerol is maintained at 5-85 wt %, specifically 10-75 wt %. When the concentration of the glycerol is too high, diglycerol, which is a dimer of glycerol, may be produced as a byproduct due to dehydration condensation of glycerol molecules. And, when the concentration of the glycerol is too low, considerable energy is needed to remove the solvent from the reaction product.

The amount of the copper-based catalyst may be 0.5-90 wt %, specifically 1-50 wt %, more specifically 3-30 wt %, based on the amount of the glycerol. When the amount of the catalyst is too large, the separation process becomes complicated because byproducts such as ethylene glycol are produced in large quantities and the preparation cost increases as the catalyst is used in excess. On the other hand, when the amount of the catalyst is too small, the selectivity and yield of 1,2-propanediol are too low, because the dehydration of glycerol proceeds but the hydrogenation does not proceed well.

Reaction temperature is 80-300° C., specifically 120-200° C. When the reaction temperature is too high, the selectivity of byproducts increase because the glycerol is decomposed and a lot of energy is needed to maintain the temperature. When the reaction temperature is too low, the selectivity and yield of 1,2-propanediol decrease because the dehydration and hydrogenation of glycerol do not proceed well.

Reaction pressure may be specifically 1-800 bar, more specifically 20-100 bar. When the reaction pressure is too high, the cost of building a reaction apparatus that can endure the high-pressure condition increases. And, when the reaction pressure is too low, the selectivity and yield of 1,2-propanediol decrease because the dehydration and hydrogenation of glycerol do not proceed well.

EXAMPLES

The present invention will be described in more detail through examples. The following examples are for illustrative purposes only and it will be apparent to those skilled in the art that the scope of this invention is not limited by the examples.

Preparation Examples

Preparation of Copper-Based Catalyst

Catalyst Preparation Example 1

(1) Preparation of $Mg_6Al_2O_8$ Metal Oxide

A metal nitrate aqueous solution was prepared by dissolving 15.7 g of magnesium nitrate and 7.6 g of aluminum nitrate in 100 mL of water and stirred at room temperature for 1 hour. In a separate container, an aqueous solution was prepared by dissolving 1 g of sodium carbonate and 6.5 g of sodium hydroxide in 150 mL of water and stirred at room temperature for 1 hour. When the aqueous solution was added dropwise to the metal nitrate aqueous solution at a rate of 10-20 mL/min, the solution turned into a white semitransparent slurry. After further stirring for about 2 hours, pH was adjusted to 9-10 by adding ammonia. After further stirring for 2 hours, the mixture was added to a 500-mL hydrothermal reactor and hydrothermal synthesis was conducted for 5 hours by raising temperature to 160° C. After the hydrothermal synthesis was completed, the obtained product was aged in an oven at 65° C. for 24 hours. After the aging was completed, the obtained product was subjected to filtration under reduced pressure to separate a precipitate, which was washed several times with distilled water of about 40° C. and then dried sufficiently in an oven at 80° C. The dried product was powdered using a mortar and sintered under air atmosphere using a combustion furnace at 900° C. for 5 hours to obtain an $Mg_6Al_2O_8$ metal oxide.

(2) Preparation of Complex Metal Oxide Structure Having Meso- and Macropores

A metal oxide dispersion was prepared by adding 4 g of the $Mg_6Al_2O_8$ metal oxide in 60 mL of ethanol and stirring for 30 minutes. In a separate container, an inorganic binder dispersion was prepared by adding 4 g of kaolin and 40 g of aluminum nitrate in 200 mL of ethanol and stirring for 30 minutes. The two dispersions were mixed and stirred at a rate of 300 rpm. Then, pH was adjusted to 9-11 by adding a 1 M sodium hydroxide aqueous solution. Then, after further stirring for 2 hours, the mixture was added to a 500-mL hydrothermal reactor and hydrothermal synthesis was conducted for 5 hours by raising temperature to 160° C. After the hydrothermal synthesis was completed, the obtained product was aged in an oven at 85° C. for 12 hours while stirring at a rate of 200 rpm. After the aging was completed, the obtained product was subjected to filtration under reduced pressure to separate a precipitate, which was washed several times with distilled water of about 40° C. and then dried sufficiently in an oven at 80° C. The dried product was powdered using a mortar and sintered under air atmosphere using a combustion furnace at 900° C. for 5 hours to obtain a complex metal oxide structure having meso- and macropores.

(3) Preparation of Copper-Based Catalyst

A copper aqueous solution prepared by dissolving 13 g of copper nitrate $(Cu(NO_3)_2 \cdot 3H_2O)$ in 2 mL of distilled water was slowly added to 5 g of the complex metal oxide structure having meso- and macropores and stirred at room temperature for 24 hours. Then, after removing water from the resulting slurry to some extent by increasing temperature to 80° C. in a water bath, water was sufficiently removed by drying in an oven at 80° C. After the drying, a catalyst wherein copper is supported on the complex metal oxide structure having meso- and macropores was prepared by sintering the same at 900° C. for 5 hours under air atmosphere.

The prepared copper-based catalyst had a formula of $Cu/Al_{5.4}Si_{1.7}$—$Mg_6Al_2O_8$ and was named as "Cu/GP-1". The catalyst had a specific surface area of 37.8 m²/g, a total pore volume of 0.34 cm³/g, an average pore size of 35.7 nm for mesopores, and an average pore size of 0.05 μm for macropores.

Catalyst Preparation Example 2

A copper-based catalyst was prepared in the same manner as in Catalyst Preparation Example 1, except that 20 g of kaolin and 40 g of aluminum nitrate were used as inorganic binders in the preparation of the complex metal oxide structure having meso- and macropores in (2).

The prepared copper-based catalyst had a formula of $Cu/Al_{12}Si_{8.3}$—$Mg_6Al_2O_8$ and was named as "Cu/GP-2". The catalyst had a specific surface area of 23.1 m²/g, a total pore volume of 0.17 cm³/g, an average pore size of 29.6 nm for mesopores, and an average pore size of 0.1 μm for macropores.

Catalyst Preparation Example 3

A copper-based catalyst was prepared in the same manner as in Catalyst Preparation Example 1, except that 40 g of kaolin and 40 g of aluminum nitrate were used as inorganic binders in the preparation of the complex metal oxide structure having meso- and macropores in (2).

The prepared copper-based catalyst had a formula of $Cu/Al_{20.3}Si_{16.6}$—$Mg_6Al_2O_8$ and was named as "Cu/GP-3". The catalyst had a specific surface area 13.8 m²/g, a total pore volume of 0.09 cm³/g, an average pore size of 25.1 nm for mesopores, and an average pore size of 0.2 μm for macropores.

Catalyst Preparation Example 4

A copper-based catalyst was prepared in the same manner as in Catalyst Preparation Example 1, except that 0.4 g of kaolin and 0.4 g of aluminum nitrate were used as inorganic binders in the preparation of the complex metal oxide structure having meso- and macropores in (2).

The prepared copper-based catalyst had a formula of $Cu/Al_{0.2}Si_{0.2}/Mg_6Al_2O_8$ and was named as "Cu/GP-4". The catalyst had a specific surface area of 17.0 m²/g, a total pore volume of 0.14 cm³/g, an average pore size of 33.0 nm for mesopores, and an average pore size of 4.1 μm for macropores.

Catalyst Preparation Example 5

A copper-based catalyst was prepared in the same manner as in Catalyst Preparation Example 1, except that 0.4 g of kaolin and 4 g of aluminum nitrate were used as inorganic binders in the preparation of the complex metal oxide structure having meso- and macropores in (2).

The prepared copper-based catalyst had a formula of $Cu/Al_{1.7}Si_{1.7}/Mg_6Al_2O_8$ and was named as "Cu/GP-5". The catalyst had a specific surface area of 16.5 m²/g, a total pore volume of 0.08 cm³/g, an average pore size of 24.2 nm for mesopores, and an average pore size of 0.9 μm for macropores.

Figure 3:
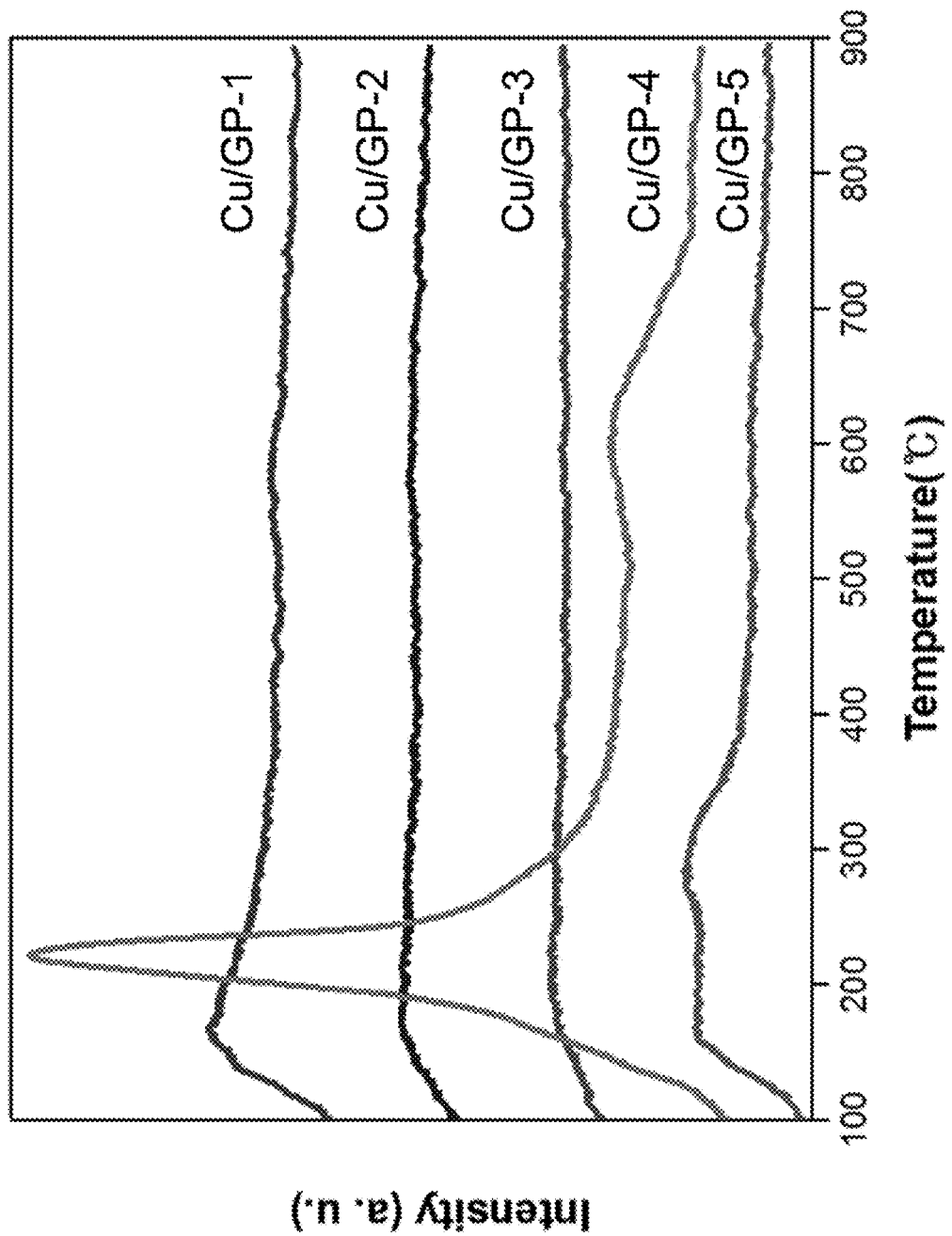
FIG. 3 illustrates a result of analyzing the basicity of copper-based catalysts prepared in Catalyst Preparation Examples 1-5 through temperature-programmed desorption measurement of $CO_2$ ($CO_2$-TPD).

FIG. 3 shows a result of analyzing the basicity of the copper-based catalysts prepared in Catalyst Preparation Examples 1-5 through temperature-programmed desorption measurement of $CO_2$ ($CO_2$-TPD). From FIG. 3, it can be seen that the Cu/GP-4 catalyst with the highest ratio of $Mg_6Al_2O_8$ exhibits the highest basicity.

The composition and physical properties of the copper-based catalysts prepared in Catalyst Preparation Examples 1-5 are summarized in Table 1.

TABLE 1

| Catalyst | Surface area (m²/g) | Total pore volume (cm³/g) | Average pore size Mesopores[1] (nm) | Macropores[2] (μm) |
|---|---|---|---|---|
| Cu/GP-1 ($Cu/Al_{5.4}Si_{1.7}$—$Mg_6Al_2O_8$) | 37.8 | 0.34 | 35.7 | 0.05 |
| Cu/GP-2 ($Cu/Al_{12}Si_{8.3}$—$Mg_6Al_2O_8$) | 23.1 | 0.17 | 29.6 | 0.1 |
| Cu/GP-3 ($Cu/Al_{20.3}Si_{16.6}$—$Mg_6Al_2O_8$) | 13.8 | 0.09 | 25.1 | 0.2 |
| Cu/GP-4 ($Cu/Al_{0.2}Si_{0.2}$—$Mg_6Al_2O_8$) | 17.0 | 0.14 | 33.0 | 4.1 |
| Cu/GP-5 ($Cu/Al_{1.7}Si_{1.7}$—$Mg_6Al_2O_8$) | 16.5 | 0.08 | 24.2 | 0.9 |

[1] Measured by nitrogen adsorption.
[2] Measured with a mercury porosimeter.

Based on the result of Table 1, the effect of aluminum (Al) and silicon (Si) as the inorganic binders adsorbed on the $Mg_6Al_2O_8$ metal oxide in forming the macropores was compared.

Upon comparison of the Cu/GP-1, Cu/GP-4 and Cu/GP-5 catalysts, it can be seen that the size of the macropores decreases as the adsorption amount of aluminum (Al) increases. When comparing Cu/GP-2 with Cu/GP-3, it can be seen that the size of the macropores increases as the adsorption amount of silicon (Si) increases. And, when comparing the Cu/GP-4 and Cu/GP-5 catalysts, the Cu/GP-4 catalyst, whose adsorption amounts of aluminum (Al) and silicon (Si) are smaller than those of the Cu/GP-5 catalyst, has macropores of a larger size. Accordingly, it can be seen that the size of the macropores is more affected by the adsorption amount of aluminum (Al) than that of silicon (Si).

Comparative Catalyst Preparation Example 1

A copper aqueous solution prepared by dissolving 1.3 g of copper nitrate ($Cu(NO_3)_2 \cdot 3H_2O$) in 2 mL of distilled water was slowly added to 5 g silica ($SiO_2$, Aldrich) and stirred at room temperature for 24 hours. Then, after removing water from the resulting slurry to some extent by increasing temperature to 80° C. in a water bath, water was sufficiently removed by drying in an oven at 80° C. After the drying, a catalyst wherein copper is supported was prepared by sintering the same at 500° C. for 5 hours under air atmosphere.

The prepared copper-based catalyst was named as "Cu/$SiO_2$". The catalyst had a specific surface area of 267.2 m²/g, a total pore volume of 0.4 cm³/g and an average pore size of 7.2 nm.

Comparative Catalyst Preparation Example 2

A copper-based catalyst was prepared in the same manner as in Comparative Catalyst Preparation Example 1, except that alumina ($Al_2O_3$, Sasol) was used as the support.

The prepared copper-based catalyst was named as "Cu/$Al_2O_3$". The catalyst had a specific surface area of 90.0 m²/g, a total pore volume of 0.1 cm³/g and an average pore size of 9.8 nm.

Comparative Catalyst Preparation Example 3

A copper-based catalyst was prepared in the same manner as in Comparative Catalyst Preparation Example 1, except that hydrotalcite ($Mg_6Al_2(OH)_{16}CO_3 \cdot 4H_2O$, Sasol) was used as the support.

The prepared copper-based catalyst was named as "Cu/MgAl". The catalyst had a specific surface area of 84.0 m²/g, a total pore volume of 0.2 cm³/g and an average pore size of 10.2 nm.

Examples

Synthesis of 1,2-propanediol

Examples 1-5 and Comparative Examples 1-3

Dehydration and hydrogenation of glycerol were conducted in a fixed-bed continuous reactor under high-pressure atmosphere using each of the catalysts prepared in Catalyst Preparation Examples 1-5 and Comparative Catalyst Preparation Examples 1-3.

A 20 wt % glycerol aqueous solution as a reactant was added to a 10-mL fixed-bed continuous reactor together with 1.0 g of the catalyst. Hydrogen was supplied into the fixed-bed continuous reactor to remove impurities in the reactor such as air. After reducing the oxide of the catalyst by pre-treating at 400° C. for 3 hours, hydrogen was injected until the internal pressure reached 25 bar. Then, the temperature of the reactor and PreHeater was slowly raised to 190° C. At this temperature, reaction was conducted for 18 hours.

The hydrogen remaining after the reaction and any gas to be produced from the reaction were analyzed using a gas chromatography system equipped with a TCD detector and a Carboshpere™ column. And, the liquid product remaining in the cylinder after the reaction and the liquid product vaporized during the reaction were analyzed using a DB-624 column equipped with an FID detector. Qualitative analysis was conducted by using a gas chromatography system equipped with an HP-5 column. From the gas chromatography analysis result, glycerol conversion rate, the selectivity and yield of products were calculated.

For each catalyst, glycerol conversion rate, product selectivity and 1,2-propanediol yield were calculated using the following equations. The result is summarized in Table 2.

Glycerol conversion rate (%)=(Moles of glycerol before reaction−Moles of glycerol remaining after reaction)/(Moles of glycerol before reaction)×100  [Equation 1]

Product selectivity (%)=(Moles of product of interest)/(Moles of total products)×100  [Equation 2]

1,2-Propanediol yield (%)=(Glycerol conversion rate)×(1,2-Propanediol selectivity)  [Equation 3]

TABLE 2

|  | Catalyst | Glycerol conversion rate (%) | Selectivity (%) | | | Yield (%) |
|---|---|---|---|---|---|---|
|  |  |  | 1,2-Propanediol | Ethylene glycol | Others* |  |
| Ex. 1 | Cu/GP-1 (Cu/Al$_{5.4}$Si$_{1.7}$—Mg$_6$Al$_2$O$_8$) | 62.3 | 97.5 | 1.1 | 1.4 | 60.7 |
| Ex. 2 | Cu/GP-2 (Cu/Al$_{12}$Si$_{8.3}$—Mg$_6$Al$_2$O$_8$) | 59.8 | 96.9 | 1.1 | 2.0 | 57.8 |
| Ex. 3 | Cu/GP-3 (Cu/Al$_{20.3}$Si$_{16.6}$—Mg$_6$Al$_2$O$_8$) | 58.0 | 96.0 | 1.1 | 2.9 | 55.7 |
| Ex. 4 | Cu/GP-4 (Cu/Al$_{0.2}$Si$_{0.2}$—Mg$_6$Al$_2$O$_8$) | 65.0 | 98.3 | 1.0 | 0.7 | 63.9 |
| Ex. 5 | Cu/GP-5 (Cu/Al$_{1.7}$Si$_{1.7}$—Mg$_6$Al$_2$O$_8$) | 60.2 | 98.1 | 1.1 | 0.8 | 59.1 |
| Comp. Ex. 1 | Cu/SiO$_2$ | 58.4 | 75.4 | 2.4 | 22.2 | 44.5 |
| Comp. Ex. 2 | Cu/Al$_2$O$_3$ | 57.0 | 93.2 | 6.2 | 0.6 | 53.2 |
| Comp. Ex. 3 | Cu/MgAl | 57.1 | 95.4 | 3.1 | 1.5 | 54.5 |

*Others: Sum of the selectivity of acetol, 1,3-propanediol, 1-propanol, 2-propanol, ethanol, methanol, etc.

As seen from Table 2, the catalysts supported on the complex metal oxide structure having meso- and macropores (Examples 1-5) showed higher selectivity for 1,2-propanediol. In particular, the Cu/GP-4 catalyst having the largest macropores showed the highest glycerol conversion rate and 1,2-propanediol yield.

Comparative Examples 1-3 showed relatively high ethylene glycol selectivity as 2.4-6.2%. The presence of the byproduct ethylene glycol causes decreased 1,2-propanediol yield and makes a 1,2-propanediol purification process complicated.

What is claimed is:

1. A copper-based catalyst for synthesis of 1,2-propanediol, wherein copper as an active metal is supported on a complex metal oxide structure having meso- and macropores represented by Chemical Formula 1, which has been prepared by coprecipitating Mg$_6$Al$_2$O$_8$ as a metal oxide having mesopores and aluminum- and silicone-based inorganic binders:

$$Al_x—Si_y—Mg_6Al_2O_8 \quad \text{[Chemical Formula 1]}$$

wherein x or y is the molar ratio of coprecipitated Al or Si per 1 mol of the Mg$_6$Al$_2$O$_8$ as a metal oxide having mesopores, x satisfying 0<x<25 and y satisfying 0<y<20.

2. The copper-based catalyst for synthesis of 1,2-propanediol according to claim 1, wherein the copper as the active metal is supported in an amount of 0.1-20 wt % based on the weight of the complex metal oxide structure.

3. The copper-based catalyst for synthesis of 1,2-propanediol according to claim 1, wherein the complex metal oxide support comprises mesopores having an average pore size of 24-36 nm and a total pore volume of 0.05-2 cm$^3$/g and macropores having an average pore size of 0.05-4.1 μm and a total pore volume of 0.05-20 cm$^3$/g at the same time.

* * * * *